(12) United States Patent
Hayes (10) Patent No.: US 6,488,831 B1
(45) Date of Patent: Dec. 3, 2002

(54) CHEMICAL SURFACE FOR CONTROL OF ELECTROOSMOSIS BY AN APPLIED EXTERNAL VOLTAGE FIELD

(75) Inventor: Mark A. Hayes, Gilbert, AZ (US)

(73) Assignee: Arizona Board of Regents Arizona State University, Tempe, AZ (US)

(*) Notice: Subject to any disclaimer, the term of this patent is extended or adjusted under 35 U.S.C. 154(b) by 0 days.

(21) Appl. No.: 09/623,233

(22) Filed: Aug. 30, 2000

Related U.S. Application Data (60) Provisional application No. 60/076,792, filed on Mar. 4, 1998, and provisional application No. 60/104,383, filed on Oct. 15, 1998.

(51) Int. Cl.[7] .................... B01D 57/02; B01D 59/42; B01D 59/50; B01D 61/42; B01D 61/58; C02F 1/469; C07K 1/26; C08F 2/58
(52) U.S. Cl. .................................................. 204/454
(58) Field of Search ................................. 204/454

(56) References Cited

U.S. PATENT DOCUMENTS

| | | | | |
|---|---|---|---|---|
| 4,680,201 A | | 7/1987 | Hjerten | ........................ 427/230 |
| 4,705,725 A | * | 11/1987 | Glajch et al. | ................ 210/656 |
| 5,074,982 A | * | 12/1991 | Novotny et al. | ............ 204/454 |
| 5,110,439 A | | 5/1992 | Holloway | .................... 204/299 |
| 5,320,730 A | * | 6/1994 | Ewing et al. | ................ 204/603 |
| 5,358,618 A | * | 10/1994 | Ewing et al. | ................ 204/603 |
| 5,576,453 A | * | 11/1996 | Buese | .......................... 556/10 |
| 5,624,539 A | * | 4/1997 | Ewing et al. | ................ 204/451 |

FOREIGN PATENT DOCUMENTS

| | | | |
|---|---|---|---|
| DE | 0107631 A2 * | 9/1983 | .......... G01N/35/08 |
| WO | 92/05433 | 4/1992 | |
| WO | 95/20157 | 7/1995 | |
| WO | 98/27418 | 6/1998 | |

* cited by examiner

Primary Examiner—Jill Warden
Assistant Examiner—Jennine Brown
(74) Attorney, Agent, or Firm—Pitney, Hardin, Kipp & Szuch LLP (57) ABSTRACT

The present invention is directed to a method for controlling electroosmotic flow by treating a surface with an organosilane having a single leaving group and optionally a ceramic oxide. This protective coating allows increased control and stabilization of electroosmotic flow by applying a radial voltage field.

13 Claims, 5 Drawing Sheets

CHEMICAL SURFACE FOR CONTROL OF ELECTROOSMOSIS BY AN APPLIED EXTERNAL VOLTAGE FIELD

CROSS-REFERENCE TO RELATED APPLICATION

This nonprovisional application claims priority to U.S. Provisional Patent Application No. 60/076,792 filed Mar. 4, 1998 and U.S. Provisional Patent Application No. 60/104,383 filed Oct. 15, 1998, both of which are incorporated by reference herein.

TECHNICAL FIELD OF THE INVENTION

This invention generally relates to electroosmotic surfaces exposed to buffers, and in particular to capillaries or channels having modified electroosmotic surfaces that are used for electrophoretic transport or separations, which permit the fall control of electroosmosis by an applied external voltage field.

BACKGROUND OF THE INVENTION

Electroosmosis is the flow of liquid that is in contact with a solid, under the influence of an applied electric field, The movement of the fluid typically results from the formation of an electric double layer at the solid/liquid interface, i.e., the separation of charge that exists in a thin layer of the surface and in a thin layer of the fluid adjacent to the surface.

Typically electroosmostic flow is observed in capillary electrophoresis which employs a capillary tube having a silica inner surface and which utilizes one or more buffer fluids. In such a configuration electroosmosis arises from interaction of the electric double layer, which is present on the inner-surface/buffer interface of a silica tube, with the longitudinal voltage gradient, wherein the electroosmotic flow rate ($v_{eof}$) is defined by the following relationship:

$$v_{eof} = \zeta(\epsilon_b/\eta) E_{app} = \mu_{eof} E_{app} \quad (1)$$

where $\zeta$ is the potential drop across the diffuse layer of the electric double layer (commonly referred to as the $\zeta$ (zeta)-potential), $\epsilon_b$ is the permittivity of the buffer solution, $\eta$ is the viscosity of the buffer solution, $\mu_{eof}$ electroosmotic mobility, and $E_{app}$ is the voltage gradient across the length of the capillary or channel. The external flow control effect is directly related to the $\zeta$-potential through the changes in the surface charge density of the channel. The total surface charge density results from the chemical ionization ($\sigma_{si}$) and the charge induced by the radial voltage field ($\sigma_{rv}$), as described in Hayes et al., "Electroosmotic Flow Control and Monitoring with an Applied Radial Voltage for Capillary Zone Electrophoresis," Anal. Chem., 64:512–516 (1992), which is incorporated herein by reference. According to the capacity model, the $\sigma_{rv}$ is described by the following equation:

$$\sigma_{rv} = (\epsilon_Q V_r / r_i)(1/\ln(r_o/r_i)) \quad (2)$$

where $\epsilon_Q$ is the permittivity of the fused silica capillary, $V_r$ is the applied radial voltage, $r_i$ is the inner radius of the capillary, and $r_o$ is the outer radius of the capillary. For a flat plate capacitor model the relationship is:

$$\sigma_{rv} = (\epsilon_Q V_r A_e)/d \quad (3)$$

where $A_e$ is the projected area of the radial electrodes on the channel wall and d is the wall thickness in the flat plate capacitor. The surface charge density is related to the $\zeta$-potential by the following equation, as described in Bard, et al., *Electrochemical Methods Fundamentals and Applications*. Wiley and Sons (New York, 1980); Davies, et al., *Interfacial Phenomena*, 2$^{nd}$ Ed., Academic Press (New York, 1963); and Overbeek, *Colloid Science*, Kruyt ed., Vol. I, p. 194 (Elsevier, Amsterdam, 1952), which are incorporated herein by reference:

$$\zeta = \exp(-\kappa x) E_{app}(\epsilon_b/\eta)(2kT/ze) \cdot \sinh^{-1}[(\sigma_{si} + \sigma_{rv})/(8kT\epsilon_b n^0)^{1/2}] \quad (4)$$

where $$\kappa = (2n^0 z^2 e^2 / \epsilon_b kT)^{1/2} \quad (5)$$

and n$^0$ is the number concentration, z is the electronic charge, e is the elementary charge, T is the temperature, $\kappa$ is the inverse Debye length, x is the thickness of the counterion, and k is the Boltzmann constant.

Areas of the capillary, which are not under direct control of the external voltage, are still effected by the radial field by a mechanism attributed to surface conductance effects, as described in Wu, et al., "Leakage current consideration of capillary electrophoresis under electroosmotic control" *J. Chromatogr.*, 652:277–281 (1993); Hayes, et al., "Electroosmotic Flow Control and Surface Conductance in Capillary Zone Electrophoresis," *Anal. Chem.*, 65:2010–2013 (1993); and Wu, et al., "Dispersion studies of capillary electrophoresis with direct control of electroosmosis," *Anal. Chem.*, 65:568–571 (1993). The magnitude of this effect may be approximated by a $\zeta$-potential averaging approach. The $\zeta$-potential in the uncovered zones is the average of the $\zeta$-potential in the controlled zones and the $\zeta$-potential from charge generated from the fused silica surface chemical equilibrium. The $\zeta$-potential for the surface chemical equilibrium may be obtained directly from flow measurements in the capillary without an applied external voltage, as described in Overbeek, at p. 194. The resulting flow ($v_{obs}$) through the capillary which is generated from these sections according to the following relationship, as described in Hayes et al., at pp.512–516:

$$v_{obs} = x' v_r + (1-x') v_{av} \quad (6)$$

where x' is the fraction of the capillary under the influence of the applied radial voltage (x'>0), $v_r$ is the electroosmotic flow rate if the entire capillary were under radial voltage effects (which may be calculated from equations 1 and 4, with 2 or 3), and $v_{av}$ is the average electroosmotic flow generated from surface charge due to chemical equilibrium and the surface charge in the controlled zone due to radial voltage effects.

The voltage gradient across the capillary also induces an additional movement of charged species according to:

$$v_{em} = (\mu_{eof} + \mu_{em}) \cdot E_{app} \quad (7)$$

where $v_{em}$ is the migration rate of a charged species, and $\mu_{em}$ is the electrophoretic mobility of that charged species. Since $\mu_{em}$ is constant under these experimental conditions, any change in $v_{em}$ may be attributed to changes in $\mu_{eof}$.

To obtain an expression directly relating changes in elution time ($\Delta t_{el}$) and the change in surface charge density ($\Delta \sigma_t$), it is noted that elution time is $t_{el} = L/v_{em}$, wherein L is the length of the capillary from the injector to the detector and $v_{em}$ is the velocity of the analyte. The velocity of the analyte is described by equation 7 where the electrophoretic mobility of that charged species is a constant under these experimental conditions. Noting that $\mu_{eo}$ is equal to $\zeta \cdot (\epsilon_b/\eta)$ (see equation 1) and the definition for $t_{el}$, the following expression can be derived:

$$t_{el}=L/[(\zeta(\epsilon_b/\eta)+\mu_{em})\cdot E_{app}]. \quad (8)$$

Equation 4 gives a function of $\zeta$ which includes a term for surface charge ($\sigma_{si}+\sigma_{rv}$) for both the chemically-generated surface charge and the external voltage-induced charge. For the surface coating assessments $\sigma_{rv}=0$ and $\sigma_{si}$ is a function of the surface coating. It follows that upon coating the surface, the measured change in elution time can be used directly to calculate the change in the surface charge from the following equation:

$$\Delta t_{el}=L/[(\{\exp(-\kappa x)\cdot(2kT/ze)\cdot\sin h^{-1}[(\Delta\sigma_{si})/(8kT\epsilon_b n^0)^{1/2}]\cdot(\epsilon_b/\eta)\}+\mu_{em})\cdot E_{app}] \quad (9)$$

or by substituting $A=\exp(-\kappa x)(\epsilon_b/\eta)(2kT/ze)$ and $B=1/(8kT\epsilon_b n^0)^{1/2}$ this simplifies to:

$$\Delta t_{el}=L/[(A\cdot\sin h^{-1}[B\Delta\sigma_{si}]+\mu_{em})\cdot E_{app}]. \quad (10)$$

Noting that all variables in this expression except $\Delta t_{el}$ are constant under these experimental conditions and rearrangement results in a more useful form of this equality:

$$\Delta\sigma_{si}=[\sin h\{([L/(\Delta t_{el}E_{app})]-\mu_{em})/A\}]/B. \quad (11)$$

However, the usefulness of the external voltage technique is limited because it only provides control at low pH (e.g., less than pH 5) and low ionic strength buffers in standard systems.

External voltage to control fluid flow at higher buffer pH can be used if the surface charge generated by the chemical equilibrium at the buffer/wall interface is minimized, as described in Hayes, et al., "Effects of Buffer pH on Electroosmotic Flow Control by an Applied Radial Voltage for Capillary Zone Electrophoresis," Anal. Chem., 65:27–31 (1993) and Poppe, et al., "Theoretical Description of the Influence of External Radial Fields on the Electroosmotic Flow in Capillary Electrophoresis," Anal. Chem., 65:888–893 (1996), which are incorporated herein by reference. Minimization of the surface charge may be accomplished with surface coatings, such as coating including organosilanes, which can minimize analyte adsorption by silica surfaces for many separation techniques, including capillary electrophoresis, as described in Poppe, et al. at pp. 888–893 and Hjerten, et al., "A new type of pH- and detergent stable coating for elimination of electroendoosmosis and adsorption in (capillary) electrophoresis," Electrophoresis, 14:390–395 (1993), which is incorporated herein by reference. Due to the labile silicon-oxygen-silicon-carbon bond (e.g., Si—O—Si—C bond) between the silica surface and the organosilane, however, such organosilane treatments have been found to be unstable at either high or low buffer pH, as described in Hjerten, et al. at pp. 390–395; Kirkland, et al., "Synthesis and characterization of highly stable bonded phases for high-performance liquid chromatography column packings," Anal. Chem., 61:2–11 (1989); and Vansant, et al., Characterization and Chemical Modification of the Silica Surface, (Elseiver, Amsterdam, 1995), which are incorporated herein by reference.

Application of coatings containing polymers to a capillary surface can also be used to eliminate the chemical equilibrium-based surface charge. As described in Srinivasan, et al., "Cross-linked polymer coatings for capillary electrophoresis and application to analysis of basic proteins, acidic proteins, and inorganic ions," Anal. Chem., 69:2798–2805 (1997), which is incorporated herein by reference, these coatings can minimize protein adsorption and eliminate or permanently change electroosmosis. Typically these polymers are covalently bound or physically adsorbed to the inner surface of the capillary, or used as dynamic coatings, i.e., buffer additives having surface-active properties so that the additives can adhere to the wall in an adsorbed/free-solution equilibrium. In addition to altering surface charge density, these polymers suppress electroosmosis by increasing viscosity within the electric double layer. Unfortunately, this local viscosity is unaffected by the potential gradients created by the external voltage fields, as described in St. Claire, "Capillary Electrophoresis," Anal. Chem, 68:569R–586R (1996). The viscosity within the electric double layer significantly contributes to the frictional forces which retard movement of the entrained ions within the longitudinal voltage gradient, thereby directly impeding electroosmotic mobility. High-viscosity surface layers, therefore, produce low electroosmosis. In fact, high viscosity surface layers have been utilized to stop electroosmosis altogether, as described in Huang, et al., "Mechanistic Studies of Electroosmotic Control at the Capillary-Solution Interface," Analy. Chem., 65:2887–2893 (1993), which is incorporated herein by reference, and Srinivasan, et al., at pp. 2798–2805. Therefore, these polymer-coated approaches cannot be utilized in systems which require dynamic flow control by an applied radial field.

This deleterious increased viscosity effect can be minimized by monolayer surface coverage without the use of polymers or polymer-forming reactants. Capillaries coated with organosilane treatments to provide monolayer surface coverage have been reported, most notably for gas and liquid chromatography applications. These treatments have also been briefly explored for radial voltage flow control for capillary electrophoresis. One example is the use of commercially 'deactivated' tubing to "... yield[s] effective EOF [electroosmotic flow] control by applied radial voltage," as described in Hayes, et al., "Electroosmotic Flow Control and Monitoring with an Applied Radial Voltage for Capillary Zone Electrophoresis," Anal. Chem., 64:512–516 (1992). Alternatively, a butylsilane monolayer surface has been used to improve the effectiveness of flow control, but resulted in a surface which was unstable above pH 5, as described in St. Claire, at pp 569R–586R; Huang et al. at pp. 2887–2893; and Towns, et al., "Polyethyleneimine-bonded phases in the separation of proteins by capillary electrophoresis," J. Chromatogr., 516:69–78 (1990), which is incorporated herein by reference. While these coatings are specifically utilized for dynamic flow control, they are also unstable at pH extremes.

Electroosmosis can be used to move fluids through the small channels of instrumentation designed on single microchips, as well as in capillary electrophoresis. One limitation of using electroosmosis for fluid flow in both these applications is the lack of control and the poor reproducibility of the electroosmotic flow in standard commercial capillary electrophoresis systems.

Accordingly, there exists a need in the art for an inner-surface coating for the external voltage control of electroosmosis having several characteristics. First, the surface created must retain low surface charge density in the presence of the aqueous buffers typically used in capillary electrophoresis. Second, the surface charge density should be insensitive to pH changes of the buffer, thus remaining consistent over a large range of normally encountered pHs (e.g., 2–11) and buffer types. Finally, the surface created must not increase the viscosity of the solution near the surface.

SUMMARY OF THE INVENTION

Accordingly it is an object of the present invention to provide an arrangement and method for controlling electroosmotic flow of a fluid which can be used over a pH range of 2–11.

It is another object of the invention to provide an arrangement and method for controlling electroosmotic flow by maintaining low charge density at the electroosmotic surface.

A further object of the invention is to provide an arrangement and method for controlling electroosmotic flow which does not result in increased viscosity in surface layers near a fluid solid interface.

These objectives have been substantially satisfied and the shortcomings of the prior art have been substantially overcome by the present invention, which in one embodiment is directed to an electrophoresis apparatus including an electroosmotic surface comprising a substrate having hydroxyl groups and a coating on the substrate comprising a component formed by reacting a triorganosilane having a single leaving group with the substrate. In another embodiment, the electroosmotic surface comprises a silica and a substrate coating comprising a sterically hindered triorganosilane having a single leaving group which has reacted with the silica substrate.

In another embodiment, the present invention is directed to an electrophoresis apparatus including an electroosmotic surface comprising a substrate having surface hydroxyl groups; a coating on the substrate comprising an inert oxide; and a coating on the oxide surface comprising a component formed by reacting an organosilane having a single leaving group with the oxide surface.

In an additional embodiment, the present invention is directed to a process for providing an electrophoresis apparatus including an electroosmotic surface comprising a substrate having hydroxyl groups and a triorganosilane coating on the surface. The process includes the step of forming a coating on the substrate by reacting a triorganosilane having a single leaving group with the substrate.

In another embodiment, the present invention is directed to a process for providing an electrophoresis apparatus including an electroosmotic surface comprising a substrate having surface hydroxyl groups, an inert oxide coated on top of the substrate, and an organosilane coated on top of the oxide surface. The process includes the step of coating the substrate with an inert oxide and then forming a coating on the oxide surface by reacting the oxide surface with an organosilane having a single leaving group.

BRIEF DESCRIPTION OF THE DRAWINGS

Further objects and advantages of the present invention will be more fully appreciated from a reading of the detailed description when considered with the accompanying drawings wherein.

DETAILED DESCRIPTION OF THE INVENTION

The present invention provides an electroosmotic surface which is modified to minimize adsorptive properties, allow dynamic control of electroosmosis with an applied external voltage field, and exhibit long-term stability in the presence of buffers over a wide pH range. Electroosmotic surface, as used herein, means any surface used for practicing electroosmosis thereon (i.e., applying an external voltage field to move a fluid), which includes, but is not limited to, solid, semi-solid, or porous surfaces made of polymers such as, oxidized poly-dimethylsiloxane, polymethyl methacrylate, PLEXIGLASS, and the like, silica, silicon, quartz, ceramics, and mixtures thereof. This modified electroosmotic surface can be utilized in many applications, which include, but are not limited to, applications utilizing small bore capillary tubes, channels, and chambers in microdevices. These applications involve the transport and/or storage of fluids for chemical reaction or analysis, such as for capillary zone electrophoresis wherein the tubing or channel bores usually have an internal diameter of less than about 200 $\mu$m. The apparatus and processes disclosed herein may also be used on microchip-based instrumentation which require control of the fluid dynamics in channels formed into or onto semiconductor devices. As used herein, the term "microchip" includes a semiconductor device comprising silica, which may be used in or in conjunction with a computer. In fact, the present invention can be useful in any device that involves fluid movement, including those devices used in science separation methods or on microinstrumentation driven by electrokinetic effects or pneumatic pumps. All of these variations and permutations are within the scope and spirit of the present invention.

In one embodiment, the present invention is directed to an electroosmotic surface comprising a substrate having hydroxyl groups, which substrate is coated. The coating comprises a component formed by the reaction of a triorganosilane having a single leaving group with the substrate. It has been surprisingly found that these organosilanes provide a stable, low surface-charge density coating which allows dynamic control of electroosmosis by an applied external field over a wide pH range.

The treatment of the surface with a triorganosilane having a single leaving group provides a low surface charge density surface which demonstrates effective dynamic control of electroosmosis at high buffer pH (e.g., up to pH 10). At such a high pH, no dynamic control is possible for untreated capillaries, as described by Poppe et al. at pp. 888–893. In addition, the magnitude of the flow control at pH 10 in coated capillaries was found to be equivalent to the most favorable buffer pH conditions, e.g., pH 3, in an untreated capillary.

Minimized adsorption of molecules is another important result of these surface treatments. Without wanting to be limited by any one theory, it is believed that the polar groups on these triorganosilanes provide a buffer-like surface that is more compatible to the solution which is in contact with the surface. This increased compatibility minimizes the differences in the energy and type of intermolecular interactions between the surface and the buffer, which are the predominant driving force for adsorption.

The triorganosilanes useful according to the present invention organosilanes are characterized by the chemical formula $R_1R_2R_3SiX$, wherein X is a leaving group selected from the group consisting of F, Cl, Br, I, At, methoxy, ethoxy, trifluoromethane sulfonate and imidazole; and $R_1$, $R_2$, and $R_3$ are individually selected from the group consisting a substituted or unsubstituted, straight chain, branched, or cyclic $C_3$–$C_{10}$ group, and a substituted or unsubstituted $C_4$–$C_{10}$ aromatic group. Preferably, the organic functional groups are selected from the group consisting of t-butyl and phenyl. Additionally, heteroatoms, such as O, N, F, S, P and B, may be substituted in these finctional groups.

In a preferred embodiment of the present invention, the electroosmotic surface includes a sterically hindered triorganosilane that is coated onto a silica substrate. Electroosmotic surfaces including such substrates typically are chemically unstable over a wide pH range because these surfaces have high charge density and high rates of buffer absorption. One example of such an electroosmotic surface is commercially available bore tubes made of silica. It has have surprisingly been found that, in addition to the benefits described above with respect to triorganosilanes, sterically hindered organosilanes demonstrate sufficient steric hindrance to minimize the acid and base catalyzed reactions at the silicon-oxygen-silicon-carbon bond between the silica surface and the hindered organosilanes. Sterically hindered organosilane, as used herein, means a reactive triorganosilane that, once reacted with n-butanol (R') to form $R_1R_2R_3SiOR'$, demonstrates a half-life of greater than 20 minutes under acidic conditions (i.e., 1% HCl by volume in ethanol corresponding to a pH of about 0.55) and greater than 10 hours under basic conditions (i.e., 5 g. of NaOH in 95 g. ethanol corresponding to a pH of about 13.9), as measured according to the method described in Cunico, et al., "The Triisopropyl Group as a Hydroxyl-Protecting Function," *J. Org. Chem.*, 45:4797–4798 (1980), which is incorporated herein by reference.

Preferred sterically hindered triorganosilanes that can be used according to the present invention include, but are not limited to, t-butyldiphenylchlorosilane, t-butyldimethylchlorosilane, triisopropylchlorosilane, and mixtures thereof. These organosilanes generally include a functional group which gives rise to a range of ion-dipole, dipole-dipole or dispersion interactions which are exhibited by many buffers that are typically used by those skilled in the art.

The sole use of triorganosilanes may not efficiently cover all of the surface charge on a surface. Without wanting to be limited by any one theory, it is believed that triorganosilanes having bulky functional groups, i.e. including at least one straight chain alkyl group which has at least six carbons or at least one branched alkyl group having at least four carbons, may not overlap or tightly fit together to form complete monolayer coverage of the electroosmotic surface. For example, after treatment with a triorganosilane having bulky functional groups and a single leaving group, a surface having silanol groups may still have some surface silanol groups exposed. Moreover, differing types of surface silanol groups, e.g., isolated, vicinal, geminal, etc., can have differing reactivities with respect to the triorganosilane. Alternate organosilane reactants, which are smaller in size, can be used to preferentially react with specific surface groups, as described in Vansant et al., *Characterization and Chemical Modification of the Silica Surface*, (Elseiver, Amsterdam, 1995), which is incorporated herein by reference. As a result, further suppression of surface charge, for both flow control and minimized adsorption, can result from using smaller organosilanes in varying proportions, such as from 0% to about 20%, with the previously described triorganosilanes.

Suitable silanes which can optionally be used in conjunction with the triorganosilanes herein according to the present invention include any organosilane that (i) has smaller organic substituents than the previously described bulky or sterically hindered triorganosilanes and (ii) a single leaving group, as hereinbefore described. Examples of such smaller silanes include, but are not limited to: trimethylchlorosilane, triethylchlorosilane, isopropyldimethylchlorosilane and mixtures thereof. These smaller organosilanes may be incorporated as an additive to a bulkier triorganosilane solution used to treat a surface, allowing competition for reactive surface sites or, alternatively, solutions containing the smaller organosilanes can be exposed sequentially to the treated surface to react with any remaining reactive surface silanol groups.

Figure 1:
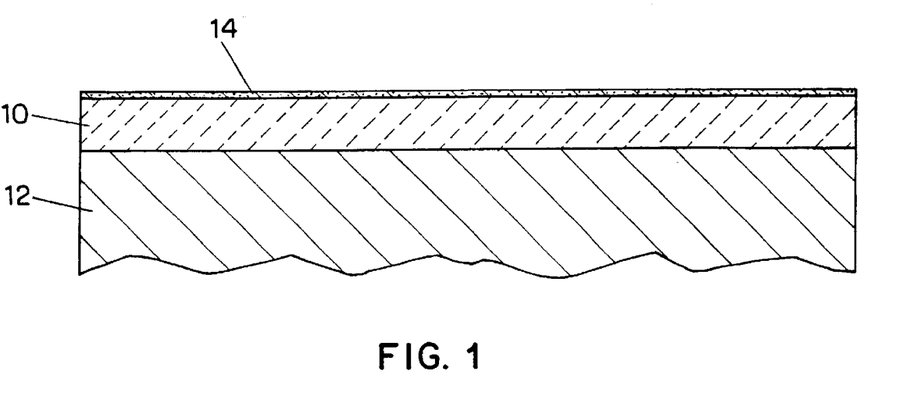
FIG. 1 illustrates a surface including a silica substrate, an inert oxide layer, and an organosilane layer according to the present invention.

In an alternate embodiment illustrated in FIG. 1, the present invention also includes providing a coating of an inert ceramic oxide layer 10 coated onto a substrate having surface hydroxyl groups 12, and coating a organosilane layer 14 onto the inert ceramic oxide layer. The ceramic oxide layer can include, but is not limited to, zirconia, titania, tantalum oxide, vanadium oxide, thoria, and mixtures thereof. In this embodiment, the ceramic oxide/organosilane layers are in fluid contact with the buffer or solution. This surface phase is effective to reduce interactions with adsorptive molecules in an adjoining buffer/solution, allow dynamic control of electroosmosis by an applied external voltage field, and provide long-term stability of the surface phase.

Specifically, organosilanes are inherently unstable when bound to certain substrates, i.e., hydrolyze, when bound to a silicate and are exposed to high or low pH buffers. While the use of hindered organosilanes on silica, as described above, result in surfaces which are stable for up to about eight weeks, ceramic oxide/organosilane layers have been found to be stable over a wide range of pH's for a considerably longer period of time, as described in Trudinger, et al., "Porous Zirconia and Titania as Packing Materials for High-Performance Liquid Chromatography," *J. of Chromotagr.*, 535:111–125 (1990); Pesek, et al., "Synthesis and characterization of titania based stationary phases using the silanization/hydrasilation method," *J. Chromatographia*, 44:538–544 (1997); Shin, et al., "Synthesis and characterization of $TiO_2$ thin films on organic self-assembled monolayers: Part I. Film formation from aqueous solutions," *J. Mater. Res.*, 10:692–698 (1995); Murayama, et al., "Reversed-Phase Separation of Basic Solutes with Alkaline Eluents on Octadecyl Titania Column," *Anal. Sci.*, 10:815–816 (1994); and Desu, "Ultra-thin $TiO_2$ films by a novel method," *Mater. Sci. Eng.*, B13:299–303 (1992), which are incorporated herein by reference.

The adsorptive properties of any electroosmotic surface depends upon the exposed functional groups, whether they are groups in an unreacted ceramic oxide, silica, or a triorganosilane. Without wanting to be limited by any one theory, it is believed that electrostatic interaction with the surface-bound charge may be the largest force contributing to adsorption. The potential for this interaction results from residual surface charge from unreacted oxide or silica. Its removal, therefore, can directly correlate to decreased flow. Surface charge is directly related to the (-potential, and therefore this surface property may be conveniently assessed by electrokinetic experiments including streaming potential and electroosmosis. The separation science technique of capillary electrophoresis provides analysis of both surface charge (i.e., through the ζ-potential) and surface adsorptive properties (i.e., by quantitating peak asymmetry). The chemistry of the surface structure which gives rise to these properties can be assessed with standard chemical surface analysis techniques.

Preparation of specific embodiments in accordance with the present invention and analysis thereof using some of these standard chemical surface analysis techniques will now be described in further detail. These examples are intended to be illustrative and the invention is not limited to the specific materials and methods set forth in these embodiments.

The examples discussed hereinafter were conducted using the following standard chemicals and instrumentation, unless otherwise stated:

Chemicals. Rhodamine 123, available from Molecular Probes (Eugene, Oreg.), t-butyldiphenylchlorosilane, available from United Chemical Technologies (Bristol, Pa.), anhydrous ethyl alcohol and HPLC grade phosphoric acid, available from Aldrich Chemical (Milwaukee, Wis.), were used as provided by the commercial suppliers. De-ionized ultra-low organic content NANOpure UV reagent grade water, available from Bamstead (Dubuque, Iowa), was used throughout the examples. Nitrogen gas was filtered through a Drierite Gas Purifier, available from W. A. Hammond Drierite (Xenia, Ohio). Rhodamine 123 sample solution was prepared by dissolving the dye in EtOH at concentrations of approximately 1 mg/ml and 1% (v/v) respectively. Electrophoretic buffers were prepared with 25 mM phosphoric acid and titrated with 1 M NaOH solution to adjust pH. All buffers were degassed and filtered with a 0.5 μm filter unit, available from Millipore (Bedford, Mass.) prior to their use.

Instrumentation. Electrophoretic separations were performed on a Crystal Series 310 Electropherograph, available from Thermo Capillary Electrophoresis (Franklin, Mass.), connected to a FD-500 fluorescence detector, available from Groton Technology (Concord, Mass.), which was operated at an excitation of 500 nm and an emission of 536 nm. External voltage was applied by a CZE 1000R high voltage system, available from Spellman High Voltage (Hauppauge, N.Y.). Fused silica capillaries, available from Polymicro Technologies Inc.(Phoenix, Ariz.) with an effective length of 44.5 cm and total length of 70 cm in 50-, 5-, and 2 μm internal diameters (i. d.) and 365-, 365-, and 150 μm outer diameters (o. d.) were respectively used, except for the external voltage experiments. Capillary tubes for the external voltage experiments were 94 cm long (68.5 cm effective length) for the uncoated experiments and 90 cm (64.5 effective length) for the coated inner-surface experiments. Data collection and processing were accomplished with a DAS 801 A/D converter at a sampling rate of 10 Hz and a personal computer running a 4880 data handling system, available from ATI Unicam (Cambridge, U.K.). All samples were injected by pressure with parameters set to produce a 1% of capillary length sample plug.

Electrophoresis was performed at 30 kV (unless indicated otherwise) and at room temperature. Radial voltage (−10 to 10 kV) was applied to a capillary wall via a three inch aluminum plate which was insulated by a plexiglass box. The box was placed between the Crystals Series 310 Electropherograph and the FD-500 fluorescence detector. The external voltage was applied 20 seconds after each run began.

EXAMPLE 1

Silica Surface Coated with a Hindered Triorganosilane

Coated capillary columns were prepared by exposing the inner surface of the capillary to a solution of 3% t-butyldiphenylchlorosilane in anhydrous methanol solution for 3–4 hours at 30–40° C. The anhydrous solution was filtered (0.5 μm) and added to the capillaries with 12-, 20-, and 35 p.s.i. of dry nitrogen gas for 50-, 5-, and 2-μm i. d. capillaries, respectively. Treated surfaces were then cured for 5–10 minutes at 110° C. or 24 hours at room temperature. Capillaries were then flushed with the buffer for 10 minutes on the Crystal 310 CE prior to use. Over the duration of 10 weeks, the tests on the treated capillaries were performed five times each day for the first three weeks and every two days thereafter. After the runs each day the capillaries were flushed with compressed air and stored. All phosphate buffers were made fresh.

The surface charge density was assessed with capillary zone electrophoresis experiments using fluorescence detection. Fluorescence detection was used because of its high detection sensitivity even with short path lengths (i.e., 2 μm, the internal diameter of the small bore capillaries). In addition, charged species, i.e, rhodamine 123, were used to assess changes in the surface charge density to obtain elution time data because neutral species would not elute without electroosmosis. The elution time, $t_{em}$, for charged analytes may be directly related to surface charge density ($\sigma_t$) according to equation 11, if $\mu_{em}$ is determined. To determine the change in surface charge density, $\mu_{em}$ need not be directly determined if other sources of altered retention, i.e., adsorption, are assumed to be negligible. In this case, $\Delta\mu_{obs}$ is assumed to be equal to $\Delta\mu_{eo}$, and $\Delta\sigma_t$, may be directly calculated therefrom via equation 11.

The inner-surface of separation tubes having an inner diameter of 50 μm were coated with t-butyldiphenylchlorosilane as described in the following chemical reaction.

Figure 2:
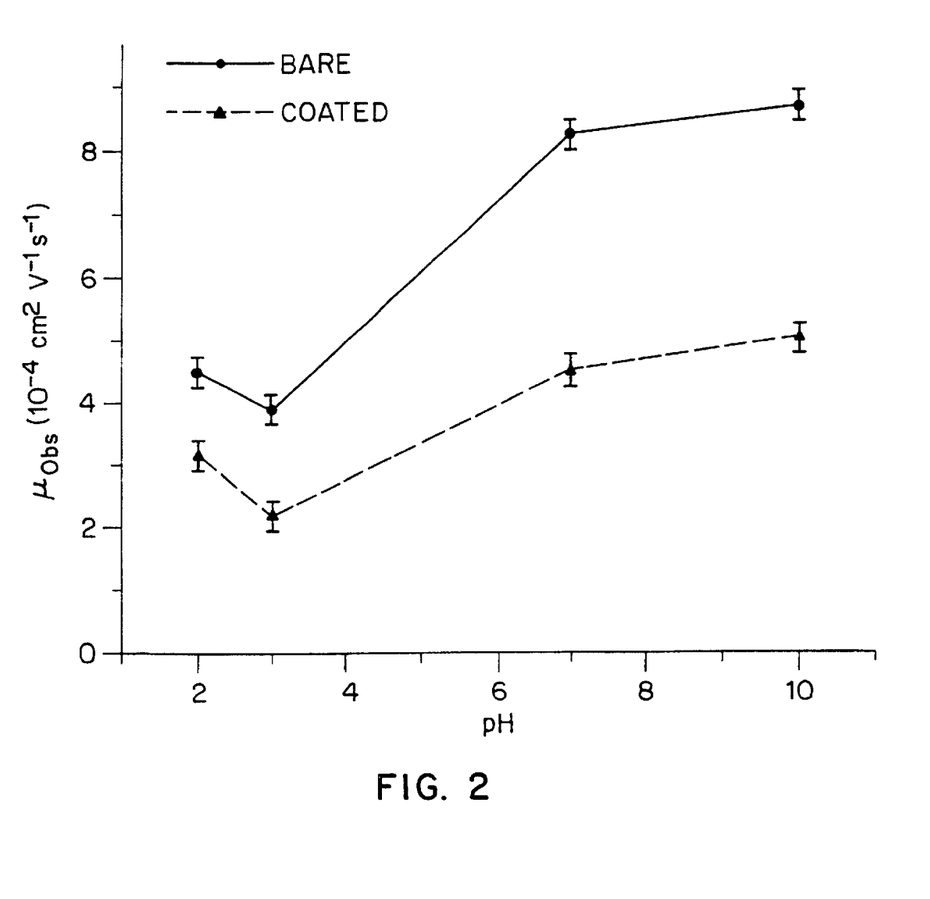
FIG. 2 is a graph of observed electrophoretic mobility versus pH for a capillary column in accordance with the invention.

The electrophoretic mobility was then observed for rhodamine 123 in the treated 50 μm i.d. columns and compared to electrophoretic mobility of the same untreated 50 µm i.d. columns. The results are illustrated in FIG. 2. The difference between $\mu_{obs}$ of uncoated and coated capillaries indicates the magnitude of the $\mu_{obs}$ suppressed by the coating, as illustrated in FIG. 2.

Figure 3:
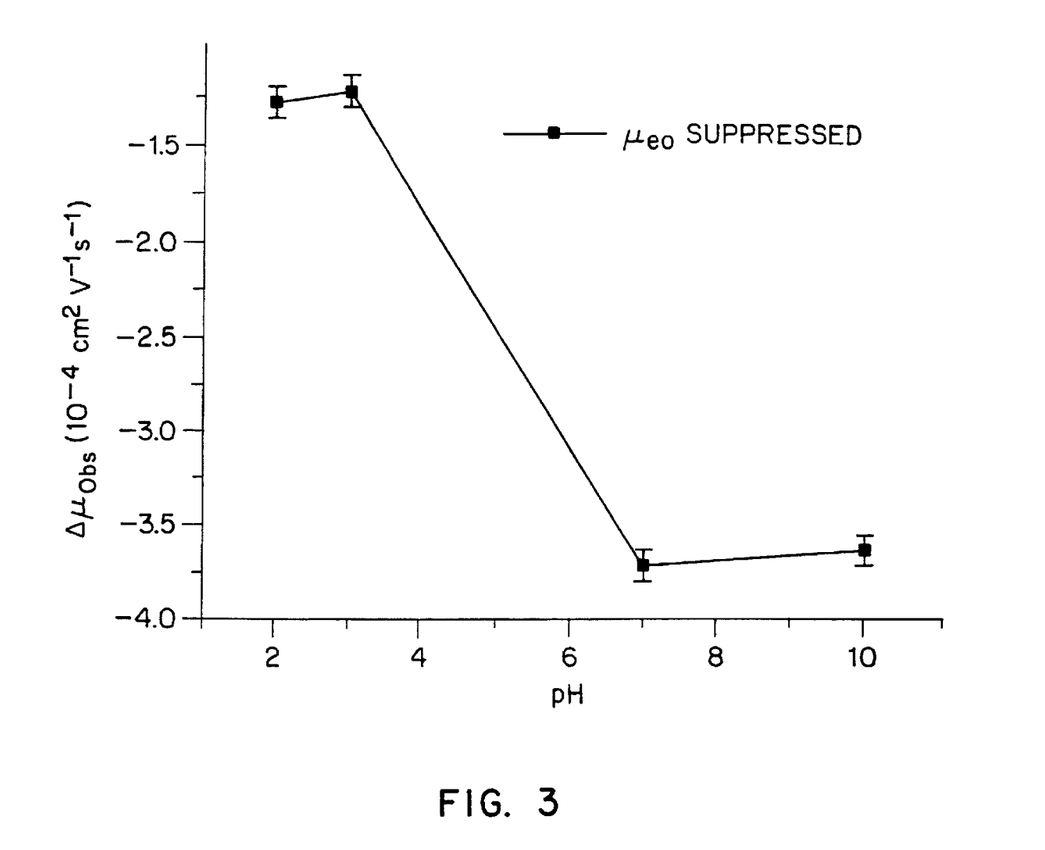
FIG. 3 is a graph illustrating suppression of electrophoretic mobility for untreated capillaries and surface treated capillaries in accordance with the invention.

As illustrated in FIG. 2, 50 µm i.d. columns coated with t-butyldiphenylchlorosilane showed a reduction of $\mu_{obs}$ of about $3.6 \times 10^{-4}$ cm$^2$/Vs and a corresponding reduction of surface charge density of about 0.075 C/m$^2$ at high pH (e.g., pH 7 and 10), which was calculated from equation 11. At low pH (e.g., pH 2 and 3) the reduction of $\mu_{obs}$ was about $1.25 \times 10^{-4}$ cm$^2$/Vs and a corresponding reduction of surface charge density of about 0.022 C/m$^2$, using equation 11, which was consistent with the reduced surface charge density of the low pH uncoated surface. The migration rate of a neutral species (methanol, data not shown) in an uncoated tube was $4.4 \times 10^{-4}$ cm$^2$/Vs (0.1 C/m$^2$), indicating that surface charge largely suppressed upon coating the tube (FIG. 3, 0.075 C/m$^2$ suppressed).

EXAMPLE 2

Small Bore Tubes Coated with a Hindered Organosilane

Figure 4:
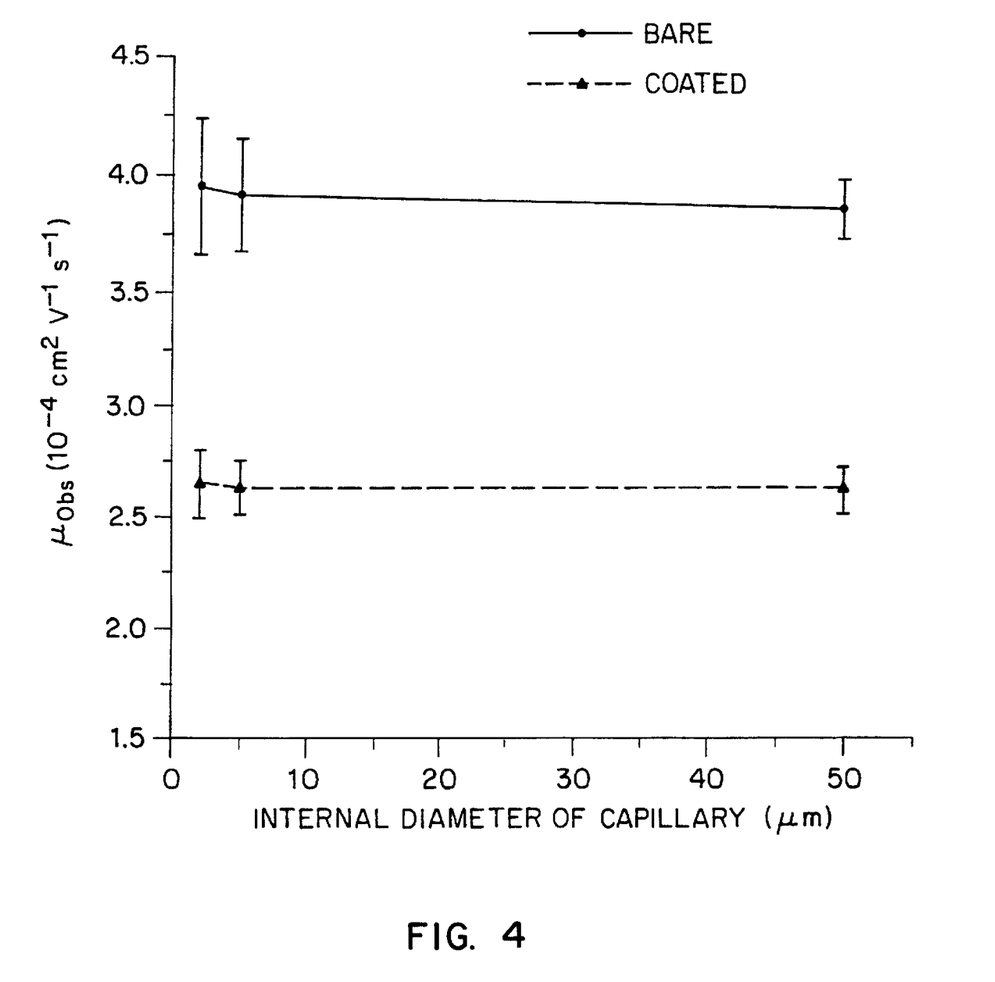
FIG. 4 is a graph of electrophoretic mobility versus internal diameter of a capillary column in accordance with the invention.

The procedure described in Example 1 was used for the coating of smaller bore tubes. The resulting electrophoretic mobility of rhodamine 123 showed a reduction of $\mu_{obs}$ by $1.2 \times 10^{-4}$ cm$^2$/Vs at pH 3.0 for all diameters tested, as illustrated in FIG. 4. These data indicate that the fabrication of coated narrow-bore tube is possible and that the behavior of these coated tubes is consistent with the performance of larger bore tubes. In addition, virtually no differences in electroosmosis was observed for varying bore diameters of coated and uncoated tubes.

EXAMPLE 3

Long Term Stability

Figure 5:
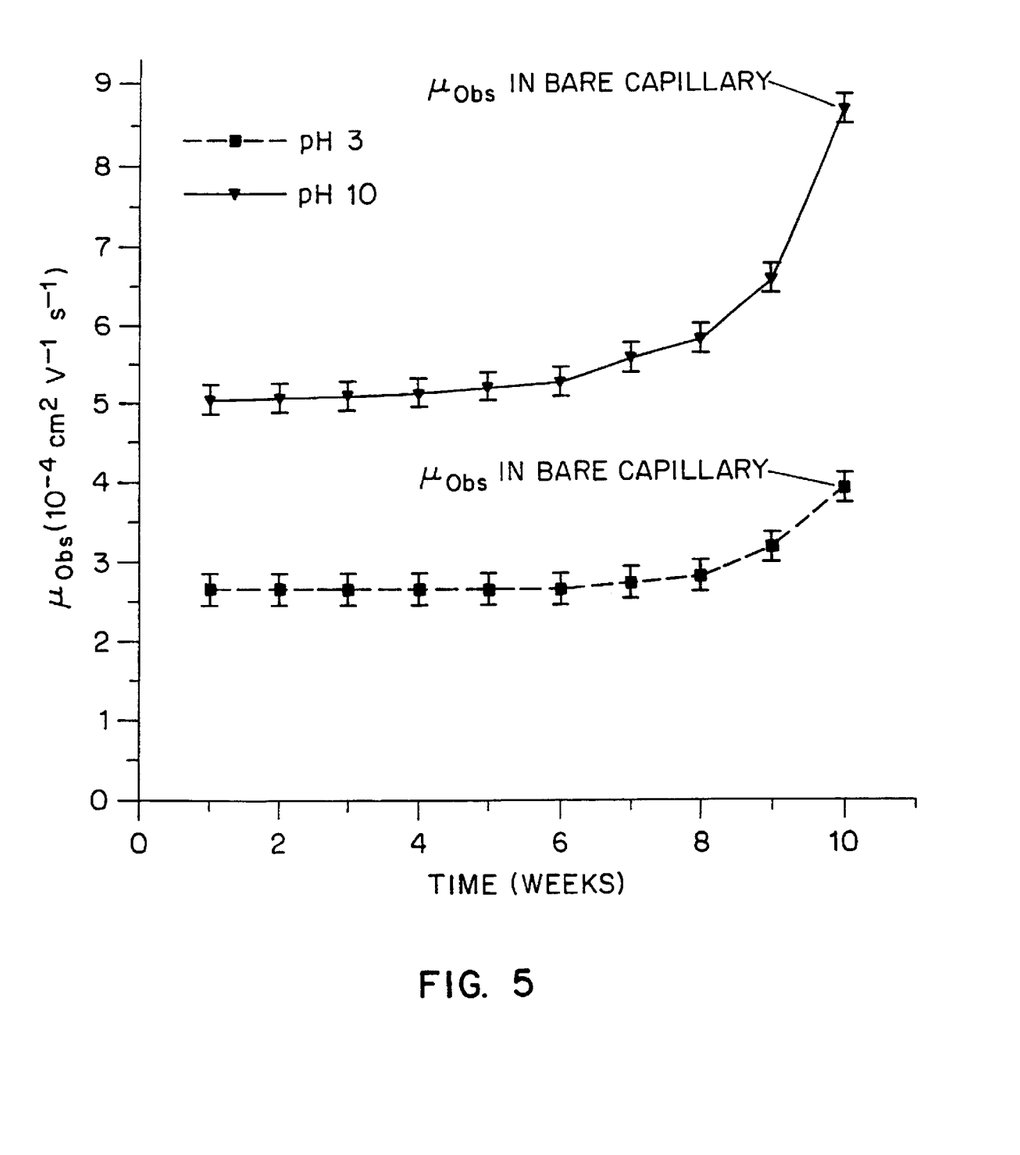
FIG. 5 is a graph of electrophoretic mobility versus time for a treated capillary in accordance with the invention.

The t-butyldiphenylchlorosilane coated 50 µm i.d. capillaries in accordance with Example 1 were also tested for stability of the observed electrophoretic mobility of rhodamine 123. The coated separation tubes were stored at a pH extreme of pH 10, and the coating remained completely stable for 8 weeks as illustrated in FIG. 3. Furthermore, the $\mu_{obs}$ remained less than about $5.5 \times 10^{-4}$ cm$^2$/Vs during the 8 weeks (i.e., the reduced surface charge density of 0.075 C/m$^2$ was maintained). At the other experimental pH extreme of pH 3, the electroosmotic measurements also indicated a stable surface with $\mu_{obs}$ remaining below $2.75 \times 10^{-4}$ cm$^2$/Vs for 8 weeks, as also illustrated in FIG. 5. After 10 weeks, the coatings apparently degraded as shown by the measured $\mu_{obs}$ increase to greater than $8.5 \times 10^{-4}$ cm$^2$/Vs for pH 10 measurements and $3.5 \times 10^{-4}$ cm$^2$/Vs for pH 3 measurements. These higher values are consistent with the uncoated capillary measurements of $8.6 \times 10^{-4}$ cm$^2$/Vs at pH 10 and $3.8 \times 10^{-4}$ cm$^2$/Vs at pH3.

EXAMPLE 4

Control of Electroosmosis Using Applied Radial Voltage Field

Figure 6:
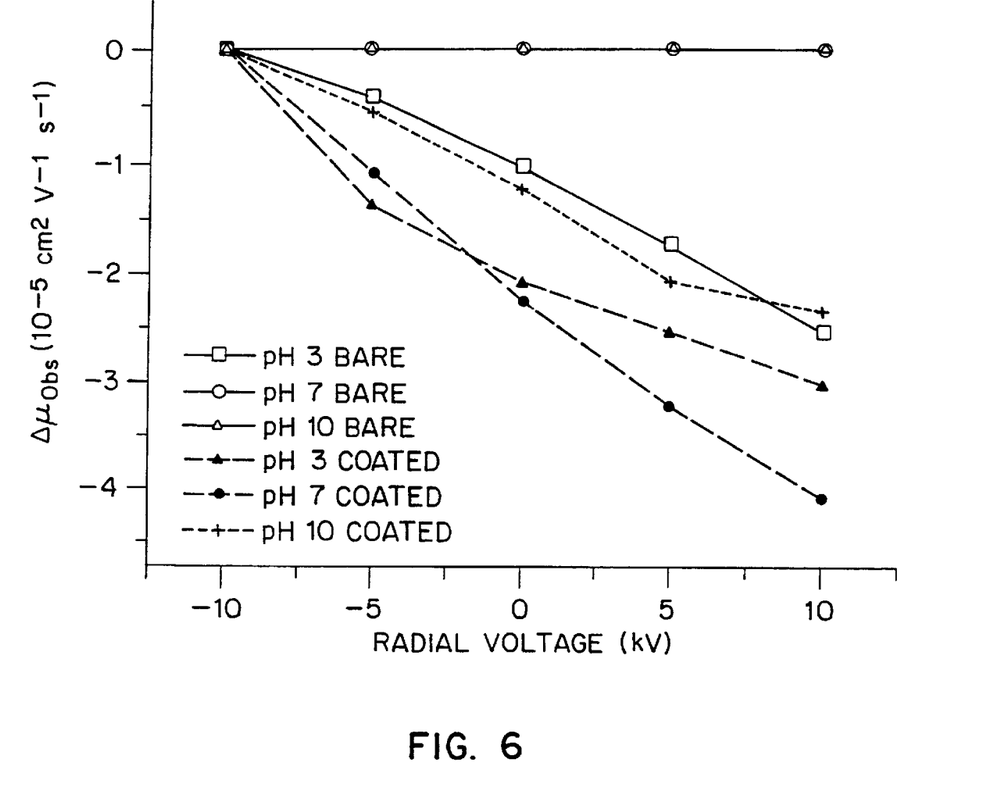
FIG. 6 is a graph of electrophoretic mobility for a capillary in accordance with the invention which is subject to an applied radial voltage field which is normalized to the −10 kV data point.

The effectiveness of controlling electroosmosis by a radial voltage field was further tested on coated tubes of 50 µm i.d./375 µm o.d. at pH 3, 7 and 10, as illustrated in FIG. 6. For application of the radial field, 8.1% of the length of the capillary was placed between two aluminum plates for which the voltage could be varied from −10 kV to +10kV. Control experiments were also performed on uncoated tubes at buffer pH of 3, 7 and 10. These control experimental results were consistent with published relationships, in that, control was demonstrated at pH 3 and no affects from the radial voltage fields were recorded with the pH 7 and pH 10 buffers, as illustrated by FIG. 6. The experiments conducted at pH 3, where $\mu_{obs}$ changed by about $2.5 \times 10^{-5}$ cm$^2$/Vs (−10 kV to +10 kV external voltage range), represent the most favorable condition for flow control in this experimental apparatus since the surface charge density from chemical equilibrium is minimized from pH effects. The physical limitations of commercially available capillary electrophoresis apparatus limit the absolute magnitude of changes in flow by an applied radial field (see Equations 1, 4, and 6) since only a small portion of the capillary was available for application of the external voltage field. This limitation, however, did not preclude the assessment of the surface chemistry of the capillaries since the pH 3 uncoated capillary experiment produced quantifiable results.

Over a large pH range, in fact from 3 to 10, the coated tubes responded to the radial voltage fields equivalent to or better than the pH 3 response with the uncoated tubes. At the extreme experimental buffer pH of 10, the change in $\mu_{obs}$ upon application of the external voltage field (−10 kV to +10 kV) was about $2.5 \times 10^{-5}$ cm$^2$/Vs, consistent with the best control of flow at low pH in unmodified capillaries. The control was even better with the same applied filed at the lower buffer pH values, $3.0 \times 10^{-5}$ cm$^2$/Vs at pH 7 and $4.0 \times 10^{-5}$ cm$^2$/Vs at pH 3. These data indicate that the surface coating diminishes the competing surface charge from buffer/surface chemical equilibria on the inner surface of the tube thus allowing full control of electroosmosis with an applied radial voltage field over a wide variety of conditions.

EXAMPLE 5

Silica Surface Coated with an Inert Ceramic Layer and Organosilanes

In this example, the inner surface of a silica capillary was coated with an inert ceramic oxide surface layer in accordance with the method as described in Desu, "Ultra-thin TiO$_2$ films by a novel method", *Mater. Sci. Eng.*, B13:299–303 (1992), which is incorporated herein by reference. A heated vacuum chamber capable of delivering TiCl$_4$, and ultrapure H$_2$O was used to develop a titania ceramic oxide layer of variable, known thickness. This chamber generally consists of a large diameter fused silica tube to house a substrate which is connected to the inlet and vacuum systems with appropriate valves. Fused quartz was dehydrated for 2 hours at 600° C. in dry flowing argon. The specimen was cooled to 100° C. and rehydrated for 10 hours with water-saturated argon. This process created a known amount of surface siloxyl functional groups, approximately $5 \times 10^{14}$ groups/cm$^2$. Subsequently, the specimen was heated to predetermined growth temperature between 100–350° C.

Before the layer was allowed to be deposited, the fused silica tube reactor was evacuated to a base pressure of $1 \times 10^{-6}$ Pa for 15 min. Then the TiCl$_4$ reactant was introduced at a vapor pressure of 200 Pa. This reactant vapor pressure was applied for 20 min., after which the sample chamber was returned to base pressure. The specimen was then exposed to 200 Pa of H$_2$O vapor for 20 min. and then returned to base pressure. Film thickness and properties were investigated as the above process constituting a single cycle.

Film thickness and refractive index of resulting TiO$_2$ films were analyzed with ellipsometry, incidence angle of 70° at wavelength of 632.8. The films were further examined with an X-ray diffractometer, electron spectroscopy for chemical analysis and Auger electron spectroscopy. Physical characterization was accomplished with optical and scanning electron microscopy.

The surface hydroxyl groups allow a two-dimensional nucleation to occur which allows a monolayer of $TiO_2$ to form for each exposure to $TiCl_4$ and subsequent hydrolysis. Growth rates per cycle is approximately 0.27 mn, allowing the thickness to be determined by the number of cycles. Oxide layers of >10.0 nm have been fabricated with this technique. This method is compatible with standard fused silica capillaries or channels on completed microdevices. $TiO_2$ may also be deposited as a step in the photolithographic fabrication of microdevices. Techniques to create these patterned oxide deposits include chemical vapor deposition (CVD) and sol-gel techniques.

Thereafter, the organosilane layer is formed on top of this inert oxide layer, as described in Example 1.

Although the invention has been described herein with respect to specific embodiments, many modifications and variations therein will readily occur to those skilled in the art. Accordingly, all such variations and modifications are included within the intended scope of this invention.

What is claimed is:

1. An electroosmotic surface, comprising:
   a substrate having surface hydroxyl groups; and
   a coating on the substrate, said coating comprising a component formed by reacting a first triorganosilane having a single leaving group with said substrate;
   wherein said electroosmotic surface is stable over a pH range of about 2 to about 11.

2. An electroosmotic surface according to claim 1, wherein said substrate is selected from the group consisting of solid surfaces, semi-solid surfaces, and porous surfaces.

3. An electroosmotic surface according to claim 2, wherein said substrate comprises a material selected from the group consisting of polymers, silica, silicon, quartz, ceramics, and mixtures thereof.

4. An electroosmotic surface according to claim 3, wherein said substrate comprises a material selected from the group consisting of oxidized poly-dimethylsiloxane, polymethyl methacrylate, silica, and mixtures thereof.

5. An electroosmotic surface according to claim 1, wherein said first triorganosilane is characterized by the chemical formula $$R_1R_2R_3SiX$$

wherein
X is a leaving group selected from the group consisting of F, Cl, Br, I, At, methoxy, ethoxy, trifluoromethane sulfonate and imidazole; and
$R_1$, $R_2$, and $R_3$ are individually selected from the group consisting of a substituted or unsubstituted, straight chain, branched, or cyclic $C_3$–$C_{10}$ group, and a substituted or unsubstituted $C_4$–$C_{10}$ aromatic group.

6. An electroosmotic surface according to claim 5, wherein said first triorganosilane is a sterically hindered triorganosilane.

7. An electroosmotic surface according to claim 5, wherein said first triorganosilane is selected from the group consisting of t-butyldiphenylchlorosilane, 2-(carbomethoxy)ethyltrichlorosilane, 3-cyanopropyltrichlorosilane, and mixtures thereof.

8. An electroosmotic surface according to claim 1 wherein said coating further comprises a component formed by reacting a second triorganosilane having a single leaving group with said substrate, wherein said second triorganosilane is smaller in size than said first triorganosilane.

9. An electroosmotic surface according to claim 1 further comprising an inert ceramic oxide layer in between the electroosmotic substrate and said coating.

10. An electroosmotic surface according to claim 9, wherein said inert ceramic oxide layer comprises a material selected from the group consisting of zirconia, titania, tantalum oxide, vanadium oxide, thoria, and mixtures thereof.

11. An electroosmotic surface according to claim 10, wherein said inert ceramic oxide layer comprises titanium dioxide.

12. An electrophoresis apparatus comprising
   a plurality of separation cappillaries, each capillary having an inlet and outlet end, the interior of each capillary being a stable electroosmotic surface in accordance with claim 1; a means for applying voltage to a plurality of separation capillaries to cause electrophoretic separation.

13. An electrophoresis apparatus comprising
   a plurality of separation capillaries, each capillary having an inlet and outlet end, the interior of each capillary being a stable electroosmotic surface in accordance with claim 9; a means for applying voltage to the plurality of separation capillaries to cause electrophoretic separation.

* * * * *